US012558127B2

(12) United States Patent
Rayes et al.

(10) Patent No.: US 12,558,127 B2
(45) Date of Patent: Feb. 24, 2026

(54) SYSTEM AND METHOD FOR ALTERING GROWTH OF BONES

(71) Applicant: Orthopediatrics Canada ULC, Vancouver (CA)

(72) Inventors: Fady Rayes, Vaudreuil-Dorion (CA); Dror Paley, West Palm Beach, FL (US); Bobby Liontis, Repentigny (CA)

(73) Assignee: Orthopediatrics Canada ULC, Vancouver (CA)

( * ) Notice: Subject to any disclaimer, the term of this patent is extended or adjusted under 35 U.S.C. 154(b) by 140 days.

(21) Appl. No.: 18/044,166

(22) PCT Filed: Sep. 3, 2021

(86) PCT No.: PCT/CA2021/051228
§ 371 (c)(1),
(2) Date: Mar. 6, 2023

(87) PCT Pub. No.: WO2022/047594
PCT Pub. Date: Mar. 10, 2022

(65) Prior Publication Data
US 2023/0310034 A1      Oct. 5, 2023

Related U.S. Application Data

(60) Provisional application No. 63/074,899, filed on Sep. 4, 2020.

(51) Int. Cl.
*A61B 17/68*        (2006.01)
*A61B 17/84*        (2006.01)
(Continued)

(52) U.S. Cl.
CPC .......... *A61B 17/683* (2013.01); *A61B 17/842* (2013.01); *A61B 2017/00477* (2013.01);
(Continued)

(58) Field of Classification Search
CPC ...................................................... A61B 17/683
See application file for complete search history.

(56) References Cited

U.S. PATENT DOCUMENTS 5,201,736 A *    4/1993   Strauss    .............. A61B 17/8071
                                                                        606/904
10,420,588 B2 *  9/2019   Murray    ................ A61B 17/842
                 (Continued)

FOREIGN PATENT DOCUMENTS

WO        2004069065 A1    8/2004
WO        2013043596 A1    3/2013
                (Continued)

OTHER PUBLICATIONS

Extended European Search Report dated Aug. 15, 2024 in the corresponding European Patent Application No. 21863165.3.
(Continued)

*Primary Examiner* — Christian A Sevilla
(74) *Attorney, Agent, or Firm* — Gerald W. Roberts; John V. Daniluck; Dentons Bingham Greenebaum LLP

(57) ABSTRACT

The present inventions relate to a system and method for altering growth of bones. More precisely, the system is an orthopedic apparatus for correcting rotational deformities and limb length discrepancies. A system of cable-couplings with linking members is used, the linking members being posts or screws traversing bones. Due to the flexibility and adaptability of the system and its components, the cable-coupling members may be installed at varying angles and locations while allowing for growth arrest or rotational corrections of said bones. A method to limit growth using cable-couplings systems is also provided.

9 Claims, 11 Drawing Sheets

(51) Int. Cl.
    *A61B 17/00*         (2006.01)
    *A61B 17/56*         (2006.01)

(52) U.S. Cl.
    CPC ............... *A61B 2017/00991* (2013.01); *A61B 2017/564* (2013.01); *A61B 2017/681* (2013.01)

(56)                 References Cited

U.S. PATENT DOCUMENTS

| | | | | |
|---|---|---|---|---|
| 2015/0216565 | A1* | 8/2015 | Paley | A61B 17/8061 |
| | | | | 606/328 |
| 2019/0357953 | A1 | 11/2019 | Venturini et al. | |
| 2020/0093514 | A1* | 3/2020 | Perez | A61B 17/683 |
| 2023/0310034 | A1* | 10/2023 | Rayes | A61B 17/683 |
| | | | | 606/328 |

FOREIGN PATENT DOCUMENTS

| | | | |
|---|---|---|---|
| WO | 2017186802 | A2 | 11/2017 |
| WO | 2018134319 | A2 | 7/2018 |
| WO | 2019152502 | A2 | 8/2019 |

OTHER PUBLICATIONS

International Search Report in the corresponding international patent application PCT/CA2021/051228 dated Nov. 12, 2021.

* cited by examiner

335

315

325

345

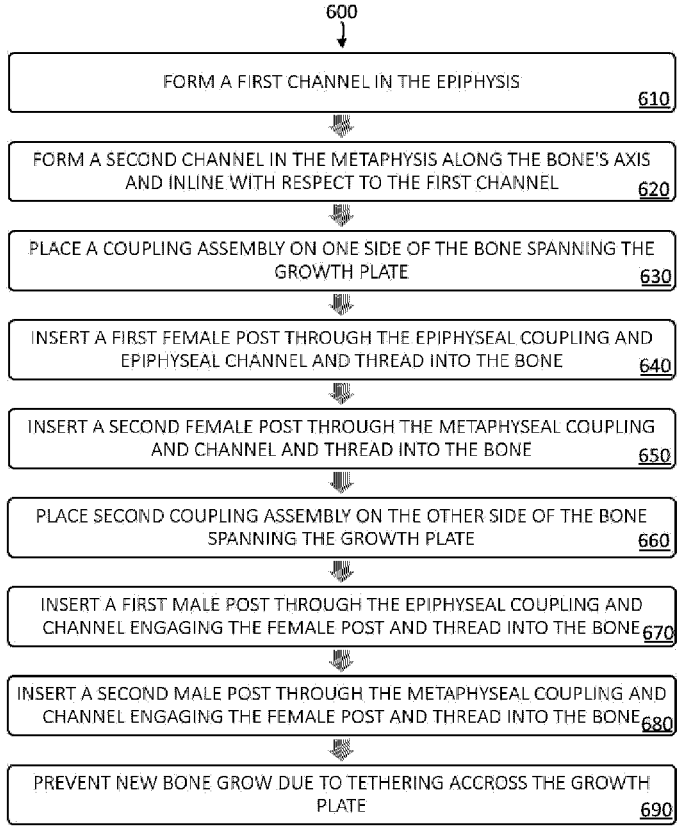

600

| FORM A FIRST CHANNEL IN THE EPIPHYSIS |
| 610 |

| FORM A SECOND CHANNEL IN THE METAPHYSIS ALONG THE BONE'S AXIS AND INLINE WITH RESPECT TO THE FIRST CHANNEL |
| 620 |

| PLACE A COUPLING ASSEMBLY ON ONE SIDE OF THE BONE SPANNING THE GROWTH PLATE |
| 630 |

| INSERT A FIRST FEMALE POST THROUGH THE EPIPHYSEAL COUPLING AND EPIPHYSEAL CHANNEL AND THREAD INTO THE BONE |
| 640 |

| INSERT A SECOND FEMALE POST THROUGH THE METAPHYSEAL COUPLING AND CHANNEL AND THREAD INTO THE BONE |
| 650 |

| PLACE SECOND COUPLING ASSEMBLY ON THE OTHER SIDE OF THE BONE SPANNING THE GROWTH PLATE |
| 660 |

| INSERT A FIRST MALE POST THROUGH THE EPIPHYSEAL COUPLING AND CHANNEL ENGAGING THE FEMALE POST AND THREAD INTO THE BONE |
| 670 |

| INSERT A SECOND MALE POST THROUGH THE METAPHYSEAL COUPLING AND CHANNEL ENGAGING THE FEMALE POST AND THREAD INTO THE BONE |
| 680 |

| PREVENT NEW BONE GROW DUE TO TETHERING ACCROSS THE GROWTH PLATE |
| 690 |

FIG. 12

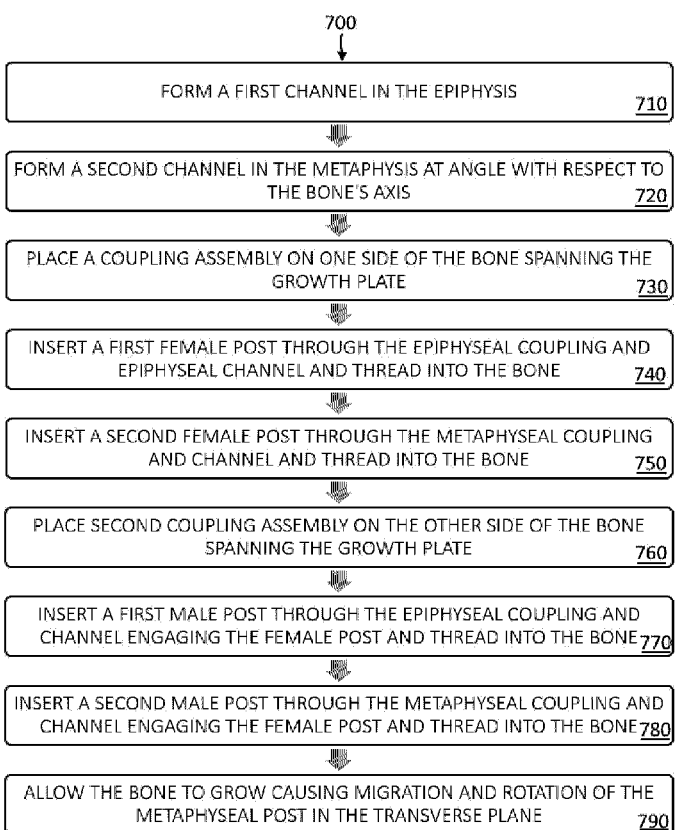

700

FORM A FIRST CHANNEL IN THE EPIPHYSIS                                          710

FORM A SECOND CHANNEL IN THE METAPHYSIS AT ANGLE WITH RESPECT TO
THE BONE'S AXIS                                                               720

PLACE A COUPLING ASSEMBLY ON ONE SIDE OF THE BONE SPANNING THE
GROWTH PLATE                                                                  730

INSERT A FIRST FEMALE POST THROUGH THE EPIPHYSEAL COUPLING AND
EPIPHYSEAL CHANNEL AND THREAD INTO THE BONE                                   740

INSERT A SECOND FEMALE POST THROUGH THE METAPHYSEAL COUPLING
AND CHANNEL AND THREAD INTO THE BONE                                          750

PLACE SECOND COUPLING ASSEMBLY ON THE OTHER SIDE OF THE BONE
SPANNING THE GROWTH PLATE                                                     760

INSERT A FIRST MALE POST THROUGH THE EPIPHYSEAL COUPLING AND
CHANNEL ENGAGING THE FEMALE POST AND THREAD INTO THE BONE                     770

INSERT A SECOND MALE POST THROUGH THE METAPHYSEAL COUPLING AND
CHANNEL ENGAGING THE FEMALE POST AND THREAD INTO THE BONE                     780

ALLOW THE BONE TO GROW CAUSING MIGRATION AND ROTATION OF THE
METAPHYSEAL POST IN THE TRANSVERSE PLANE                                      790

FIG. 13

SYSTEM AND METHOD FOR ALTERING GROWTH OF BONES

CROSS-REFERENCE TO RELATED APPLICATIONS

The present patent application claims the benefits of priority of U.S. Provisional Patent Application No. 63/074, 899, entitled "SYSTEM AND METHOD FOR GUIDING GROWTH OF BONES" and filed at the United States Patent and Trademark Office on Sep. 4, 2020, the content of which is incorporated herein by reference.

FIELD OF THE INVENTION

The present invention generally relates to the field of pediatric orthopedic apparatuses and, in particular, to an orthopedic apparatus and related method for correcting rotational deformity and limb length discrepancy.

BACKGROUND OF THE INVENTION

Epiphysiodesis is a pediatric orthopedic surgery procedure that aims at altering or stopping bone growth naturally occurring through a growth plate, also known as the physeal plate. Epiphysiodesis can be temporary or permanent.

Temporary hemiepiphysiodesis is generally known as guided growth surgery or growth modulation surgery. Temporary hemiepiphysiodesis works by stopping or inhibiting the physeal growth at one hemi-side of the growth plate. In consequence, the other hemi-side is allowed to grow normally and unhindered. This process occurs gradually and steadily and eventually leads to correction of the angular deformity in most cases. Temporary hemiepiphysiodesis is reversible, i.e. the device used to achieve epiphysiodesis can be removed after the desired correction is achieved and the growth plate can thus resume its normal growth and function. On the other hand, permanent epiphysiodesis is irreversible and the growth plate function cannot be restored after surgery.

Temporary epiphysiodesis is widely used to treat angular or coronal plane deformities around the knee in children, i.e. deformities occurring in the medial/lateral plane as genu varum/genu valgum. Additionally, it has been used to treat sagittal plane deformities, i.e. deformities arising in the anterior/posterior plane. However, current devices are not well adapted to treat rotational deformities (transverse plane) or to reliably treat limb length discrepancy through growth arrest.

Rotation Deformities

In orthopedics, rotational deformities of the bone along the lower portions of an individual can change the planar orientation of various respective reference planes for the hip, knee, and ankle. For example, abnormal angulation of the femoral neck with respect to the transcondylar axis of the knee is referred to as femoral anteversion or femoral retroversion. In general, rotational deformities as discussed above may be defined as an abnormal angulation of a bone relative to a longitudinal axis.

It is very common in infants to be born with femoral anteversion due to the position of the fetus inside the womb and can occur in up to 10% of children. In fact, femoral anteversion is the most common cause of children, older than 3 years of age, walking with their toes inward (in-toeing). Although most rotational bone abnormalities, such as femoral anteversion, are resolved under normal growth and development, a small percentage of cases will continue to suffer from a residual rotational deformity that may later require surgical correction.

One common surgical method of bone realignment to address femoral anteversion is by performing an osteotomy procedure that requires a cutting of the bone followed by its realignment to the correct orientation. However, osteotomy procedures require a relatively large incision to access the bone for the surgeon to perform the bone cutting and realignment, thereby making the procedure substantially invasive. In addition, the procedure can cause disruption of the surrounding musculature as well as possibly damaging the adjacent neurovascular structures. Procedures to cut and realign bones are associated with a long and painful rehabilitation period that can last several months. The cut bone ends may not heal and, in such cases, further surgery may be necessary. Implant failure is also a well-documented complication of osteotomies. Another concern is the accidental damage to the growth plate that can occur during the surgical realignment procedure, which can later inhibit healthy and normal limb growth. In addition, there are still further concerns, including the risk of infection, as well as the risk of delayed union of the bone segments, mal-union of the bone segments, and over/under correction. As such, current surgical bone realignment methods and apparatuses require a relatively invasive procedure in order to perform rotational bone deformity correction.

An alternative to invasive osteotomies is the use of guided growth, through minimally invasive devices. These devices can address angular deformities but none are designed to treat rotational bone deformities.

Limb Length Discrepancy

Lower extremity length inequality is a complex problem that is frequently seen by pediatric orthopaedic surgeons. Limb length discrepancy (LLD) may result in gait abnormality, pain, early arthritis of the hip, and pelvis and spine issues. Management of LLD requires an understanding of the mechanisms and concepts of growth, including the relationships among age, maturity, and leg length. Management options range from shoe lift to surgical intervention (epiphysiodesis, shortening osteotomy, and/or limb lengthening) depending on the magnitude of the discrepancy and other patient factors.

Several surgical techniques for permanent epiphysiodesis about the knee have been described including transphyseal screws and physeal ablation. The timing of permanent epiphysiodesis is critical; it is generally done close to skeletal maturity, calculated such that remaining growth of the short leg will closely approximate the discrepancy. Ill-timing of epiphysiodesis could result in overcorrection or under-correction. Combined with its low complication rate and minimally invasive approach, temporary epiphysiodesis is therefore an attractive solution for the treatment of LLD. However, current devices are ill-adapted for this procedure and have not been shown to be effective.

U.S. Pat. No. 10,682,161 B2 discloses a system to limit growth of bones using linking plates via rods located above and below a growth plate. The length of the rods disclosed in U.S. Pat. No. 10,682,161 B2 patent are not adjustable due to the connection elements of the components being treaded. The system disclosed comprises non-adjustable connection elements and rigid plates, thus, the resulting system is not accommodating to different anatomies of bones. Furthermore, this patent does not disclose center-to-center length adjustability between fasteners or the rod holes. Therefore, axis-to-axis distance has to be precisely predetermined for every plate.

The U.S. Pat. No. 9,877,755 B2 discloses a length adjustable rod, or post, connected to a plate that spans the bone above and below the growth plate and from cortex to cortex. This system, while improving the adjustability of previous U.S. Pat. No. 10,682,161 B2, still lacks flexibility as the rods may only be moved in a predetermined axis. Furthermore, the plates used may also not fit on all shapes of bones due to their shape and rigidity.

The US patent application no. US 2019/0357953 A1 discloses a system comprising a pair of holding elements linked by a flexible central portion for epiphysiodesis. The holding elements are fastened to bones through threaded connections. The system of the said patent application differs from U.S. Pat. No. 7,811,312 B2 as the system uses locking screws. Even if the system of the said patent application does not comprise rigid plates, the threaded connection between the fastening elements and the holding elements is rigid. The rigid threaded connections between holding elements and fasteners results in an undesirable normal (perpendicular) force applied to the fasteners with respect to the holding elements. Similarly to the U.S. Pat. No. 10,682,161 B2 patent, a center-to-center length adjustability between the fasteners is not disclosed. Thus, the axis-to-axis distance has to be precisely predetermined for each holding element.

There is thus a need for a system and method for altering growth of bones that have a low complication rate and a minimally invasive approach. Preferably, there is a need for systems and methods for treating both rotational bone deformities and limb length discrepancies which may overcome the shortcomings of the above-mentioned prior art documents.

SUMMARY OF THE INVENTION

The aforesaid and other objectives of the present invention are realized by generally providing a method and system for altering growth of bones.

In a first embodiment of the invention, an orthopedic fixation device for altering growth of a bone to be used with a growth plate is provided, the device comprising: one bicortical post assembly; and two coupling assemblies, each coupling assembly comprising two retaining portions, at least one of the retaining portions being adapted to receive and engage an extremity of the post assembly, each coupling assembly being positionable on a side of the bone and being adapted to flexibly conform with the side of the bone.

In another aspect of the invention, the bicortical post assembly may be telescopic. The bicortical post assembly may comprise two bicortical posts. A first of the two bicortical posts may be slidable into a second of the two posts. A first of the two bicortical posts may be a male component and a second of the two bicortical posts may be a female component, the male component slidingly and freely engaging into the female component. The male and female components may freely rotate in relation to one another.

In another aspect of the invention, the bicortical post may comprise a cortical threaded portion adjacent to the post assembly retaining portion. Each bicortical post may comprise a cannulation for guidance over wire. Each bicortical post may comprise a head portion adapted to engage with the post retaining portion. The head portion may freely rotate when inserted in the post retaining portion.

In another aspect of the invention, each bicortical post may comprise a drive feature for insertion into the bone using a tool. The tool may be a hex tool.

In another aspect of the invention, each coupling assembly may comprise two coupling members flexibly attached to one another. The coupling members may be attached to one another via a flexible tether. The coupling members may move freely along the flexible tether. The flexible tether may be a flexible cable. The flexible cable may be made of any one of the following materials: metal, plastic, polymer, elastomer or a combination thereof. Each coupling member may comprise one of the post retaining portions. The post retaining portions may comprise an opening for receiving and engaging a head portion of one of the posts.

In another aspect of the invention, the position of the coupling assemblies may be mirrored from one another in view of the center of the growth plate. Each coupling assembly may be at an angle about a substantially vertical plan between the two said coupling assemblies.

In another aspect of the invention, the device may stop the vertical growth of the bone.

In another aspect of the invention, the device may comprise two bicortical post assemblies. A second of the retaining portions may be adapted to receive and engage an extremity of the second post assembly. The two bicortical post assemblies may not be parallel to one another or being unparallel to one another.

In another aspect of the invention, a second of the retaining portions may be adapted to receive and engage a bone screw.

In another embodiment of the invention is provided a coupling assembly positionable on a side of a bone, the coupling assembly comprising: two couplings, each coupling comprising an aperture for receiving a bone fastening element; and a flexible tethering member linking the two couplings for the two couplings to be positioned to conform to the side of the bone. The aperture may be adapted to receive a head of the bone fastening element. The aperture may allow free rotation of the head of the fastening element. Each of the couplings may further comprise tethering apertures for receiving the flexible tethering member. The coupling apertures may allow free translation of the flexible tethering member. The coupling assembly may further comprise at least one crimping element for securing the flexible tethering member to the two couplings. The at least one crimping element may be a sphere secured to an end of the flexible tethering member and may have physical dimensions preventing passage through the tethering apertures.

In another aspect of the invention, the flexible tethering member may be a cable. The cable may be made of any one of the following materials: metal, plastic, polymer, elastomer or a combination thereof.

In another embodiment of the invention is provided a method for correcting limb length discrepancy or a deformity of a bone using a growth plate, the method comprising: placing a first coupling assembly on one side of the bone to flexibly conform with the side of the bone; placing a second coupling assembly on the other side of the bone to flexibly conform with the side of the bone; passing two first fixing elements through in retaining portions of the first coupling assembly; passing two second fixing elements through two retaining portions of the second coupling assembly; threading the fixing elements to the bone above or under the growth plate.

In another aspect of the invention, the method may further comprise: inserting one of the two first fixing elements in a first channel in the epiphysis of the bone above or below the growth plate, the inserted first fixing element being a first post; inserting one of the two second fixing elements in the first channel from the opposite side of the bone from the first coupling assembly, the inserted second fixing element being a second post; and sliding a first of the first and second posts into a second of the first and second posts.

In another aspect of the invention, the method may further comprise: inserting the other of the two first fixing elements in a second channel in the epiphysis of the bone on the opposite side of the growth plate of the first channel, the other of the two first fixing elements being a third post; inserting the other of the two second fixing elements in the second channel from the opposite side of the bone from the first coupling assembly, the other of the two second fixing elements being a fourth post; and sliding a first of the third and fourth posts into a second of the third and fourth posts.

In another aspect of the invention, the two first fixing elements may be screws. The two second fixing elements may be screws.

In another aspect of the invention, the method may further comprise forming a channel in the epiphysis of the bone above or below the growth plate.

Additional objectives, advantages and novel features will be set forth in the description which follows or will become apparent to those skilled in the art upon examination of the drawings and detailed description which follows.

The features of the present invention which are believed to be novel are set forth with particularity in the appended claims.

BRIEF DESCRIPTION OF THE DRAWINGS

The above and other objects, features and advantages of the invention will become more readily apparent from the following description, reference being made to the accompanying drawings in which:

FIG. 12 is a flow chart illustrating a method for using an orthopedic device for growth arrest in accordance with the principles of the present invention.

FIG. 13 is a flow chart illustrating a method for using an orthopedic device for the correction of rotational deformity in accordance with the principles of the present invention.

DETAILED DESCRIPTION OF THE PREFERRED EMBODIMENT

A novel method and system for guiding growth of bones will be described hereinafter. Although the invention is described in terms of specific illustrative embodiment(s), it is to be understood that the embodiment(s) described herein are by way of example only and that the scope of the invention is not intended to be limited thereby.

Figure 1:
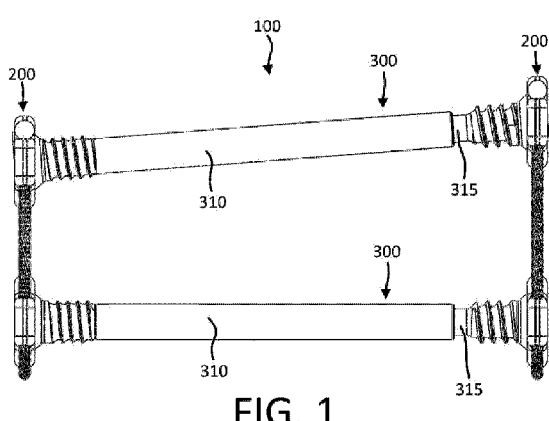
FIG. 1 is a front view of an embodiment of a device assembly for guiding growth of bones in accordance with the principles of the present invention, the device assembly being shown with two cable-coupling assemblies and two post assemblies.
Figure 7:
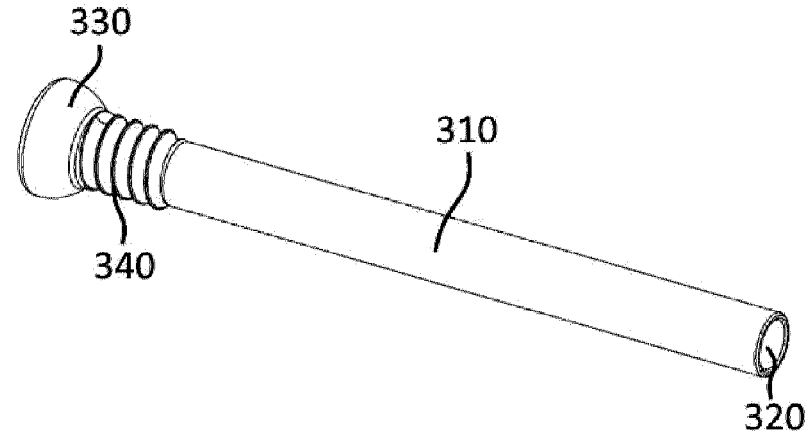
FIG. 7 is a perspective view of a female post component of the post assembly of [FIG. 5].
Figure 8:
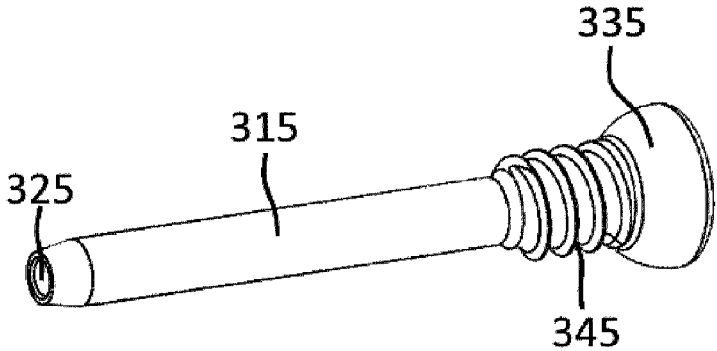
FIG. 8 is a perspective view of a male post component of the post assembly of [FIG. 5].

Referring to [FIG. 1], an embodiment of an orthopedic device assembly 100 is illustrated. The orthopedic device assembly 100 comprises two cable-coupling assemblies 200 and two post assemblies 300. Each of the post assemblies 300 further comprises a female post 310, post member or component (also shown in [FIG. 7]) and a male post, post member or component 315 (also shown in [FIG. 8]).

Each of the female 310 and male 315 posts generally include a semi-spherical or conical head 330 and 335, respectively, designed to engage a mating surface in the cable-coupling assembly 200. One of the advantages of having a spherical or conical mating between the posts 310 and 315 and the cable-coupling assemblies 200 is that it allows for non-parallel placement of the metaphyseal posts or cortical screws with regards to the epiphyseal ones. Such non-parallel placement generally aims at allowing more surgical flexibility and at allowing a lower profile and a better contouring of the bone.

Figure 2:
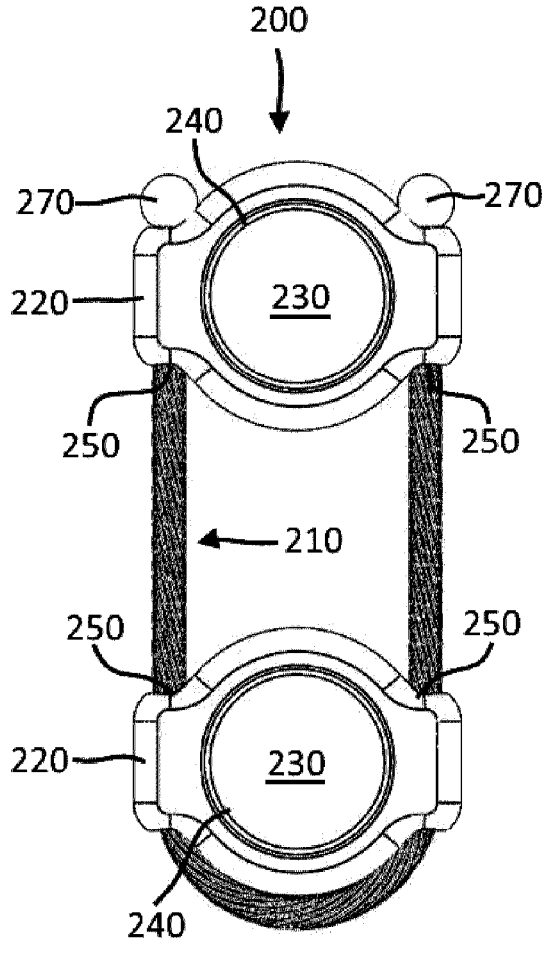
FIG. 2 is a front view of an embodiment of a cable-coupling assembly with a fixed cable length in accordance with the principles of the present invention.
Figure 3:
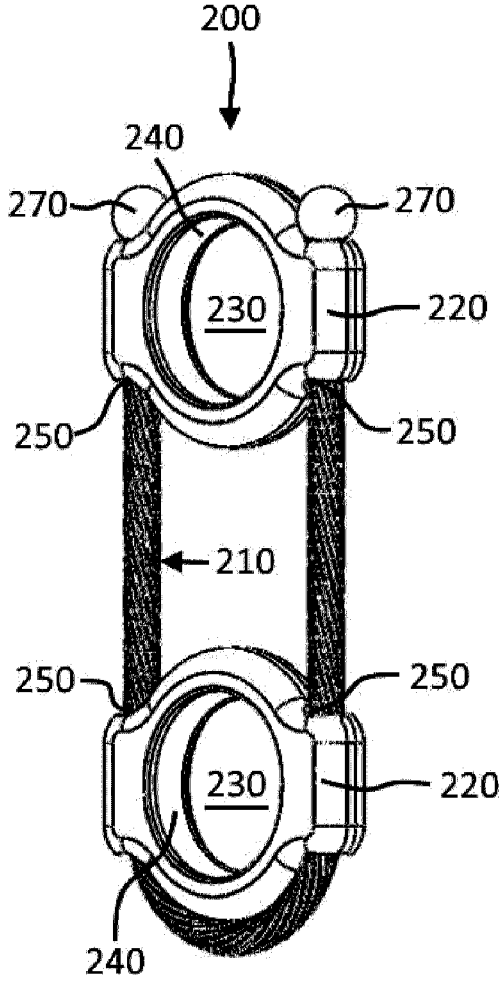
FIG. 3 is a perspective view of the cable-coupling assembly of [FIG. 2].
Figure 5:
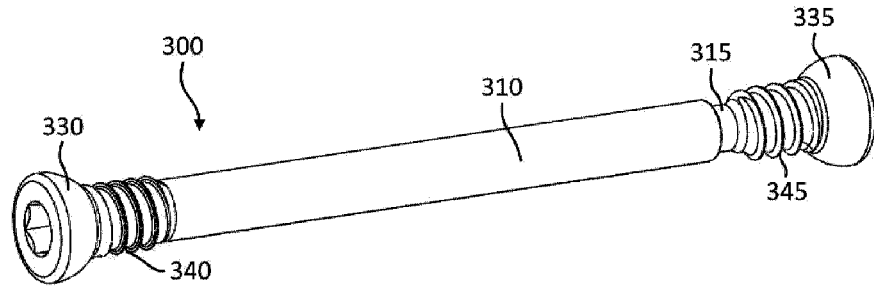
FIG. 5 is a perspective view of an embodiment of a post assembly of the device assembly, the post assembly comprising female and male components.
Figure 6:
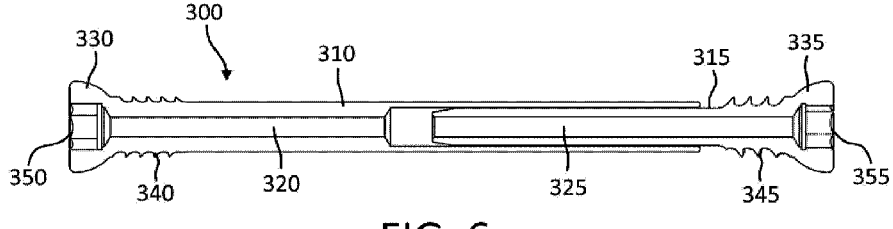
FIG. 6 is a cross-sectional view of the post assembly of [FIG. 5].

FIGS. 2 and 3 show a cable-coupling assembly 200 wherein FIGS. 5 and 6 show a post assembly 300.

Now referring to FIGS. 2 and 3, an embodiment of a cable-coupling assembly 200 is illustrated. The cable-coupling assembly 200 comprises a tethering member 210 and two or more couplings, or coupling members, 220. The coupling 220 includes an aperture, or opening or post retaining portion, 230 generally adapted to receive and hold a fastening element such as, but not limited to, the head of a screw or a post. The perimeter of the aperture typically comprises a mating surface 240, such as a shape mating with the coupling, such as a poly-axial spherical mating surface. Each side of the coupling 220 further comprises a passage or aperture 250 adapted to receive the tethering member 210 (e.g. multifilament cable). Understandably, each of the passages 250 may be shaped and positioned at different locations on the coupling 220 to allow passage of the tethering member 210.

In some embodiments, the tethering member 210 may be flexible, such as being made of any material that exhibits some level of flexibility to follow and/or accommodate unique bone geometries and contours. For example, the tethering member 210 may be made of metal, plastic, polymer, elastomer, any other suitable materials, or any combination thereof. In addition, depending on the intended use of the tethering member 210, the length, width, and thickness of the tether may be varied.

Figure 4:
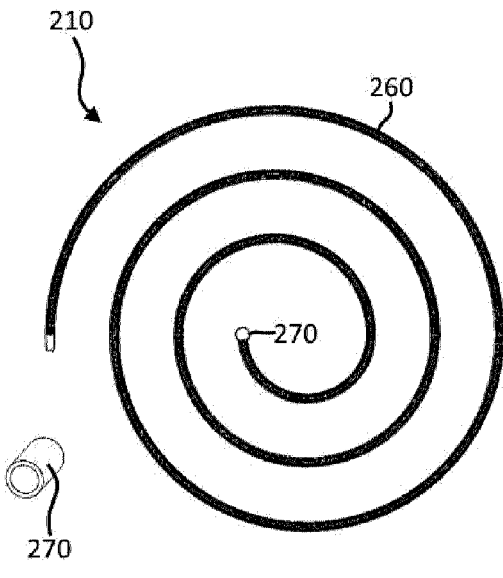
FIG. 4 is an illustration of a multifilament cable and of a crimp in accordance with the principles of the present invention.

Now referring to [FIG. 4], the tethering member 210 is embodied as one continuous cable 260 including a crimping component or mechanical fitting 270. In such embodiment, the cable-coupling assembly 200 may be assembled at time of surgery by passing the cable 260 through the passages 250 and by retaining the said cable 250 in the coupling 220, for example by crimping the cable 260 with a crimp 270.

In some embodiments, a method to install the cable-coupling assembly 200 comprises placing the couplings 220 at the ideal anatomical position before tethering together the epiphyseal coupling 220 to the metaphyseal coupling 220 spanning the growth plate. In some embodiments, the cable 260 may then be crimped at the desired length and the excess cable 260 may be cut off. The couplings 220 generally remain slideable along the cable 260.

Referring back to FIGS. 2 and 3, in yet another embodiment, the continuous cable 260 is pre-assembled to the two couplings 220 at pre-determined lengths and secured via mechanical fittings such as beads, ball clasps or sleeve crimps 270.

Now referring to FIGS. 5 to 8, the post assembly 300 may comprise a female 310 and a male component 315. The male component 315 is adapted to slide in and out of the female component 310. Moreover, the male component 315 may also be adapted to freely rotate inside the female component 310 as to allow independent rotation and advancement of components 310 and 315 into the bone. The female 310 and male 315 components typically share a central channel (cannulation) 320 and 325, respectively, used to guide the components 310 and 315 with the help of a guide wire (not shown).

The female 310 and male 315 components may include a head 330 and 335, respectively, at an extremity, the heads 330 and 335 being adapted to engage the mating surface 240 of the coupling 220. The heads 330 and 335 may have varying shapes allowing the engagement to the mating surface 240, such as but not limited to a semi-spherical shape as shown in embodiments of FIGS. 7 and 8.

The slideable mating between the female 310 and male 315 components may allow for exact length adjustment to the cortex-to-cortex distance of the post assembly 300 during insertion of said components 310 and 315. Moreover, the components may remain free to telescope after their implantation, allowing for elongation or collapse of said components even when the bone geometry changes over time.

The female 310 and male 315 components may further comprise a threaded extremity 340 and 345, respectively, adapted to engage the bone portion. In such embodiments, the head is adapted to engage the coupling 220. Each component 310 and 315 may include a recessed drive feature 350 and 355, respectively.

Figure 9:
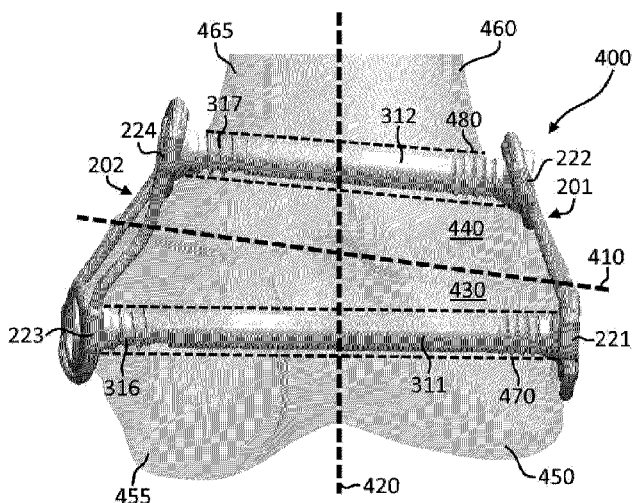
FIG. 9 is a front view of an embodiment of a device assembly for guiding growth of bones in accordance with the principles of the present invention, shown installed in bone, spanning a growth plate and configured to cause growth arrest.

Now referring to [FIG. 9], for the purpose of causing temporary bone growth arrest, an embodiment of the orthopedic device 400 may be positioned to cover the span of a growth plate in a configuration where, in the sagittal view, the cable-coupling assembly 200 is placed along a bone's longitudinal axis 420. This tethering across the growth plate generally prevents further axial growth, thus causing a temporary growth arrest.

Figure 10:
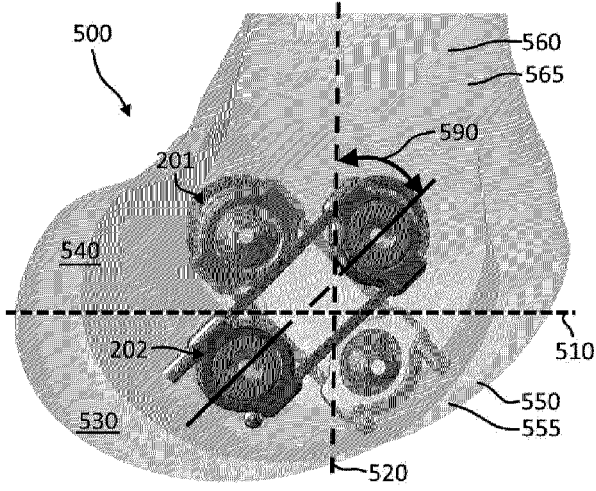
FIG. 10 is a side view of an embodiment of a device assembly for guiding growth of bones in accordance with the principles of the present invention, shown installed in bone, spanning a growth plate and configured to cause derotation.
Figure 11:
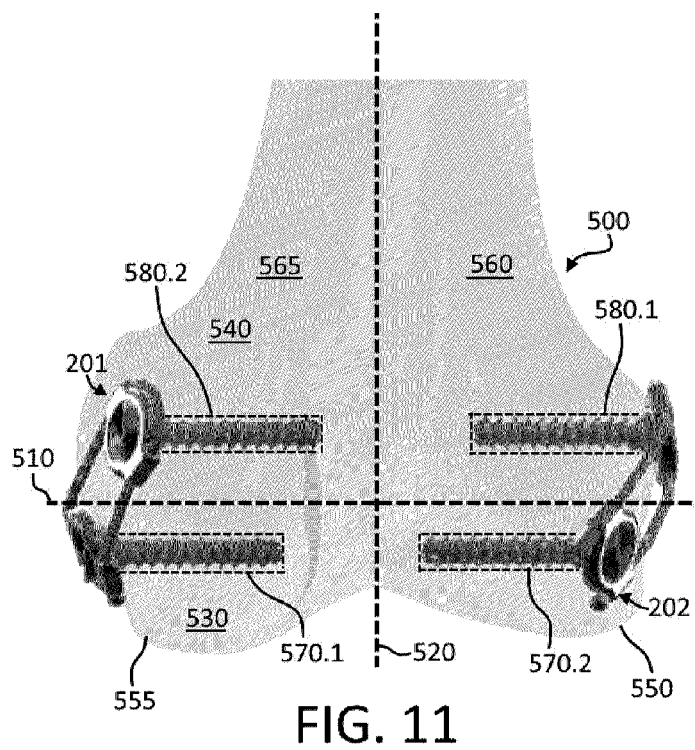
FIG. 11 is a front view of an embodiment of a device assembly for guiding growth of bones in accordance with the principles of the present invention, the device assembly being shown in bone spanning a growth plate and configured to cause rotation and is using cortical screws as fasteners.

Referring to FIGS. 10 and 11, for the purpose of correcting rotational deformity, an embodiment of the orthopedic device 500 wherein the cable-coupling assemblies 200, similar to embodiments shown in FIGS. 2 and 3, can be placed to span a growth plate in a configuration where, in the sagittal view, the cable-coupling assemblies are placed at an angle 590 with respect to the anatomical bone axis 520 and that the medial and lateral implant assemblies 201 and 202 are placed at a mirrored angle 590 to the axis 520 (forming an 'X'). The cable-coupling assemblies 200 may be linked or fixed to the bone via orthopedic fasteners such as, but not limited to, posts or cortical screws.

Alternatively, in another embodiment (not shown), the cable-coupling assembly may be linked to the bone via a post assembly 300. The angular tethering of the growth plate may lead to rotation in transverse plane as axial growth occurs.

The present disclosure further provides methods to temporarily prevent bone growth or to correct unwanted rotational deformities. The methods may be used with any embodiment of the orthopedic apparatus 100 presented above, but are not limited therein.

Referring now to [FIG. 12], a method 600 for using an orthopedic device for growth arrest 400, such as the device shown in [FIG. 9] is illustrated. The method 600 comprises forming a first channel 470 in the epiphysis 430, 610, forming a second channel 480 in the metaphysis 440 along the growth plate plane 410 and inline with respect to the first channel 470, 620, placing a cable-coupling assembly 201 on one side of the bone spanning the growth plate 410, 630 and, inserting a first female post 311 through the epiphyseal coupling 221 and epiphyseal channel 470 and thread into a section of the bone 450, 640. The method 600 may further comprise inserting a second female post 312 through the metaphyseal coupling 222 and channel 480 and thread into a section of the bone 460, 650. The method 600 may further comprise placing a second cable-coupling assembly 202 on the other side of the bone spanning the growth plate 410, 660, inserting a first male post 316 through the epiphyseal coupling 223 and channel 470 engaging the female post 311 and thread into a bone portion 455, 670 and inserting a second male post 317 through the metaphyseal coupling 224 and channel 480 engaging the female post 312 and thread into a bone portion 465, 680. The method 600 generally aims at preventing new bone growth due to the tethering the growth plate 690.

Referring now to [FIG. 13], a method 700 for using an orthopedic device to correct rotational deformity 500 as seen in FIGS. 10 and 11 is provided. The method 700 generally allows the bone to grow while causing migration and rotation of a metaphyseal post assembly, comprised of posts 312 and 317, in the transverse plane 790. The method 700 comprises forming a first channel 570 in the epiphysis 530, 710, forming a second channel 580 in the metaphysis 540 at an angle 590 with respect to the bone's axis 520, 720 and placing a cable-coupling assembly 201 on one side of the bone spanning the growth plate 510, 730. The method 700 further comprises inserting a first female post 311 through the epiphyseal coupling 221 and the formed epiphyseal channel 570 and threading into the bone 550, 740 and inserting a second female post 312 through the metaphyseal coupling 222 and formed channel 580 and threading into the bone 560, 750. The method 700 further comprises placing a second cable-coupling assembly 202 on the other side of the bone spanning the growth plate 510, 760, inserting a first male post 316 through the epiphyseal coupling 223 and on the other side of the formed channel 570 engaging the female post 311 and threading into the bone 555, 770 and inserting a second male post 317 through the metaphyseal coupling 224 and on the other side of the formed channel 580 engaging the female post 312 and threading into the bone 565, 780. It can be appreciated that any one of the cable-coupling assemblies 201 and 202 may be installed before the other cable-coupling assembly. It can further be appreciated that posts 311, 312, 316 and 317 may be replaced by any other type of fasteners, such as screws in which case there may be two epiphyseal channels 570.1 and 570.2 and two metaphyseal channels 580.1 and 580.2.

Understandably, the orthopedic device 100 may be adapted to be installed in any type of bone requiring growth restriction.

In some embodiments, the insertion of female and male posts may be replaced by the insertion of fasteners such as screws.

While illustrative and presently preferred embodiment(s) of the invention have been described in detail hereinabove, it is to be understood that the inventive concepts may be otherwise variously embodied and employed and that the appended claims are intended to be construed to include such variations except insofar as limited by the prior art.

The invention claimed is:

1. An orthopedic fixation device for altering growth of a bone to be used with a growth plate, the device comprising:
    a first bicortical post assembly comprising two telescopic monocortical posts, a first of the two monocortical posts being slideable and rotatable into a second of the two monocortical posts; and
    two coupling assemblies, each coupling assembly comprising two retaining portions, at least one of the retaining portions being adapted to receive and engage an extremity of the first bicortical post assembly, each coupling assembly being positionable on a side of the bone and being adapted to flexibly conform with the side of the bone;

each coupling assembly comprising two coupling members flexibly attached to one another by a flexible tether;
    wherein the coupling members are freely movable along the flexible tether.

2. The device of claim 1, wherein the first of the two monocortical posts is a male component and the second of the two monocortical posts is a female component, the male component being slideable and freely rotatable into the female component.

3. The device of claim 1, each of the monocortical posts comprising a cortical threaded portion adapted to be adjacent to one of the retaining portions of one of the coupling assemblies.

4. The device of claim 1, each of the monocortical posts comprising a cannulation for guidance over a wire.

5. The device of claim 1, each of the monocortical posts comprising a head portion adapted to engage with one of the retaining portions of one of the coupling assemblies.

6. The device of claim 5, wherein one of the head portions is configured to be inserted into one of the retaining portions of one of the coupling assemblies and is freely rotatable therein.

7. The device of claim 1, wherein the positions of the coupling assemblies are mirrored from one another relative to the center of the growth plate.

8. The device of claim 1, wherein the device is configured to stop the vertical growth of the bone.

9. The device of claim 1, further comprising a second bicortical post assembly.

\* \* \* \* \*